(12) United States Patent
Beckers et al.

(10) Patent No.: US 9,640,292 B2
(45) Date of Patent: May 2, 2017

(54) X-RAY APPARATUS

(71) Applicant: PANalytical B.V., Almelo (NL)

(72) Inventors: Detlef Beckers, Almelo (NL); Stjepan Prugovecki, Almelo (NL)

(73) Assignee: PANALYTICAL B.V., Almelo (NL)

(*) Notice: Subject to any disclaimer, the term of this patent is extended or adjusted under 35 U.S.C. 154(b) by 237 days.

(21) Appl. No.: 14/547,976

(22) Filed: Nov. 19, 2014

(65) Prior Publication Data

US 2015/0200030 A1 Jul. 16, 2015

(30) Foreign Application Priority Data

Jan. 15, 2014 (EP) .................................... 14151339

(51) Int. Cl.
| | |
|---|---|
| *G01T 1/36* | (2006.01) |
| *G21K 1/04* | (2006.01) |
| *G01N 23/201* | (2006.01) |
| *G01N 23/207* | (2006.01) |

(52) U.S. Cl.
CPC ........... *G21K 1/046* (2013.01); *G01N 23/201* (2013.01); *G01N 23/207* (2013.01)

(58) Field of Classification Search
CPC ....... G01N 23/20; G01N 23/201; G21K 1/062
See application file for complete search history.

(56) References Cited

U.S. PATENT DOCUMENTS 6,226,349 B1 * 5/2001 Schuster ............... G01N 23/20
378/81
2003/0112923 A1 6/2003 Lange et al.

FOREIGN PATENT DOCUMENTS

| EP | 1 396 716 | 3/2004 |
|---|---|---|
| EP | 1 912 061 | 4/2008 |
| GB | 2 266 040 | 10/1993 |
| KR | 2009/0046598 | 5/2009 |
| WO | WO 2011/139473 | 11/2011 |

OTHER PUBLICATIONS

Herbert; "A new flat Goebel-mirror for the optimization of the primary beam in Bragg-Brentano diffraction geometry"; Microstructure Analysis in Material Science; Jun. 17, 2005.

* cited by examiner

*Primary Examiner* — Courtney Thomas
(74) *Attorney, Agent, or Firm* — Leason Ellis LLP

(57) ABSTRACT

X-ray diffraction apparatus includes a flat graded multilayer 8 which may be used in a SAXS configuration for a sample 6. The apparatus may be adapted for Bragg-Brentano measurements by a collimator 16 without the need for alternate beam paths or complex arrangements.

12 Claims, 3 Drawing Sheets

X-RAY APPARATUS

CROSS REFERENCE TO RELATED APPLICATIONS

This application claims priority under 35 U.S.C. §119 to European Patent Application EP14151339.0, filed Jan. 15, 2014, which is hereby incorporated by reference in its entirety herein.

FIELD OF INVENTION

The present invention relates to apparatus for X-ray diffraction and methods for X-ray diffraction measurements.

BACKGROUND TO THE INVENTION

X-ray diffraction apparatus is used in a variety of contexts and applications.

One application is for the measurement of powder samples.

In particular, small angle X-ray scattering, SAXS, may be used to measure X-ray scattering at small angles which corresponds to features of the sample at length scales which may be for example between 1 nm and 100 nm. The small angles (2θ) used in SAXS are typically less than 5°. The smaller the angle, the larger the length scale and hence the larger the particle size, or pore size in porous materials, may be.

A beam of X-rays is typically collimated down to a very thin beam (a line) or a small spot directed to a powder sample. The X-rays scattered by the sample at small angles are detected by an X-ray detector.

For some SAXS methods it is important to work with quasi-monochromatic radiation, because it improves the normalization possibilities of the data (for higher accuracy data. Normalization may be carried out when the background from the sample holder is subtracted from the sample signal. A first measurement is carried out by measuring the sample in a sample holder and a second measurement is carried out by measuring the sample holder alone. The results are scaled and normalised and the second measurement results are subtracted from the first measurement results to get the clean contribution to the results from the sample.

It is important for accurate SAXS measurements that the collimator does not create additional disturbing scatter radiation that may influence the SAXS results.

One approach that was formerly used was to use a higly polished collimation block that blocked most of the intensity from an X-ray tube and left only a very thin beam path to hit the sample. A high quality of the collimation block was required to prevent additional scatter.

More recent set-ups for SAXS have used 1- or 2-dimensional multilayer pre-collimators to create some pre-collimation in front of a final collimator, which consists, for example, of slits or pinholes. The different types of collimators (1D or 2D) ensure that measurements down to small angles (2θ) are possible and disturbing scatter radiation that may influence the SAXS results is removed.

The pre-collimation by a 1- or 2-dimensional multilayer pre-collimator has two effects. Firstly, the pre-collimation renders the X-ray beam monochromatic. More importantly, the pre-collimation typically acts to increase the intensity of the X-ray beam by collecting and redirecting the beam from the X-ray tube before it arrives at to the collimator. The pre-collimator normally uses a parabolic or elliptically shaped mirror for one or two dimensional collimation.

Apparatus for carrying out SAXS measurement is commercially available.

Purchasers of X-ray diffraction apparatus prefer not to have to buy multiple pieces of equipment to carry out different measurements, nor to carry out extensive work to reconfigure apparatus for different measurement techniques. There would therefore be an advantage in providing an instrument that can carry out such additional types of measurement with minimal reconfiguration and in particular using the same apparatus as may be used for SAXS.

SUMMARY OF THE INVENTION

According to a first aspect of the invention, there is provided X-ray diffraction apparatus, comprising
  an X-ray source having a focus;
  a sample stage;
  a flat graded multilayer between the focus and the sample stage for directing X-rays from the focus onto the sample stage; and
  an X-ray detector for detecting X-rays from a sample mounted on the sample stage;
  further comprising a collimator located between the X-ray source and the sample stage, wherein the collimator is adjustable to a wide effective aperture for Bragg-Brentano measurements or to a narrow effective aperture for SAXS.

The inventors have realised that by replacing an elliptical or parabolic mirror in some existing SAXS apparatus by a flat graded multilayer then the apparatus can additionally be used for Bragg-Brentano measurements.

A flat graded multilayer has a plurality of layers and a flat surface. The function of such a flat graded multilayer is as a monochromator for divergent optics. An incoming divergent X-ray beam, for example from an X-ray source, is incident on a planar graded multilayer, and reflects monochromatic light in such a way that the reflected monochromatic light has the same divergence as the incoming beam.

Thus, flat graded multilayers have previously been used in applications where a diverging beam is required. SAXS on the other hand requires a beam collimated as accurately as possible, with no or only a very small divergence, and so the use of a flat graded multilayer in SAXS apparatus has not previously been proposed, as far as the inventors are aware.

in spite of this apparent disadvantage, the inventors have found that SAXS measurements carried out using a flat graded multilayer are as good as those using conventional apparatus, as illustrated below, and that the equipment can produce additionally improved and high quality Bragg-Brentano results.

The narrow effective aperture may be used for SAXS, and may additionally be used for reflectometry measurements or for other measurements using such an aperture, for example micro-spot analysis on inhomogeneous samples.

The narrow aperture for SAXS or other measurements may result in a beam divergence angle of no greater than 0.07°, preferably no greater than 0.05°. The wide effective aperture for Bragg-Brentano may typically result in a beam divergence larger than 0.1°, preferably greater than 0.15°.

Further developments of the invention are the subject-matter of the dependent claims.

In preferred embodiments, there is no need to add an additional optic such as a monochromator on the secondary side or exchange an optic on the primary side to carry out multiple measurement types.

The collimator may be located between the flat graded multilayer and the sample stage. This allows X-rays from the X-ray source to impact on the flat graded multilayer at a large range of angles since there is no collimator between the flat graded multilayer to keep the flat graded multilayer at a distance from the source. Alternatively, the collimator may be located between the X-ray source and the flat graded multilayer.

The collimator may be a one dimensional collimator, for example a slit aperture of variable width.

The collimator may also be a two-dimensional collimator having an aperture of variable width and/or height.

The apparatus may further comprise a further flat, parabolic, elliptical or hyperbolic shaped multilayer arranged between the flat graded multilayer and the sample stage.

The X-ray detector may be a position sensitive detector. The position sensitive detector may be a one-dimensional detector detecting position in one direction or a two dimensional detector having pixels arranged in a two dimensional matrix.

In another aspect, the invention relates to a method of operation of X-ray diffraction apparatus according to any preceding claim, comprising:
  adjusting the collimator to a wide effective aperture and carrying out measurements in a Bragg-Brentano geometry; and
  adjusting the collimator to a narrow effective aperture and carrying out small angle X-ray scattering, SAXS, measurements.

The method may additionally include carrying out reflectometry measurements using a narrow effective aperture.

BRIEF DESCRIPTION OF THE DRAWINGS

An example of the invention will now be described with reference to the accompanying diagrams, in which.

DETAILED DESCRIPTION

Figure 1:
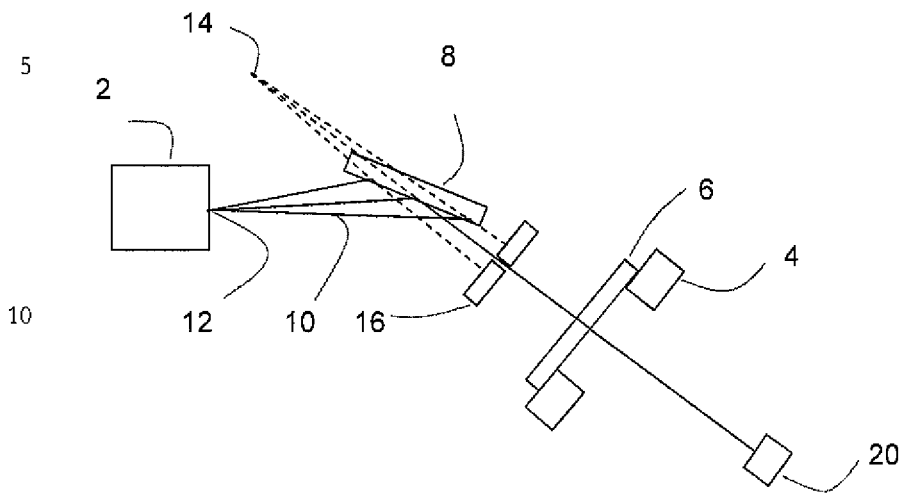
FIG. 1 is a schematic diagram of an arrangement for SAXS measurement according to an embodiment of an apparatus according to the invention.

Referring to FIG. 1, apparatus according to the invention includes an X-ray source 2, a sample stage 4 for mounting a powder sample 6 and an X-ray detector 20.

A flat graded multilayer 8 is provided in the path of a beam 10 between the X-ray source 2 and the sample stage 4.

A line focus 12 of the source creates a diverging X-ray beam 10 which is incident on the flat graded multilayer 8 which reflects monochromatic light onto a sample 6 on the sample stage 4. The flat graded multilayer 8 does not change the divergence of beam 10 and hence the sample is illuminated as if it were from apparent focus 14.

The apparatus also includes a collimator 16 in the incident beam path 10 between source 2 and sample stage 4.

To carry out SAXS measurement, the source 2, sample 6 on sample stage 4 and detector 20 are arranged as in FIG. 1 with the beam 10 restricted to a narrow range of angles, no broader than 0.07°, by collimator 16. The apparent focus 14, sample 6 and detector 20 are arranged in an approximate straight line and the detector is used to detect small angle scattering by the sample 6.

The measurement is then repeated without the sample 6, just with stage 4 and sample holder, and the results normalised. The repeated measurement is subtracted from the first measurement to calculate the scattering of the sample 6.

The collimator 16 may be in particular a slit collimator arranged between the flat graded multilayer 8 and the sample stage 4. The slit may be adjusted widely from a first state (full lines, FIG. 2) in which a broad X-ray range is passed and a second state (dashed lines, FIG. 2) which restricts the X-rays to a narrow range of angles.

Such a collimator can collimate the incident X-ray light down so that the resultant beam can be used for SAXS measurements or reflectometry.

Figure 2:
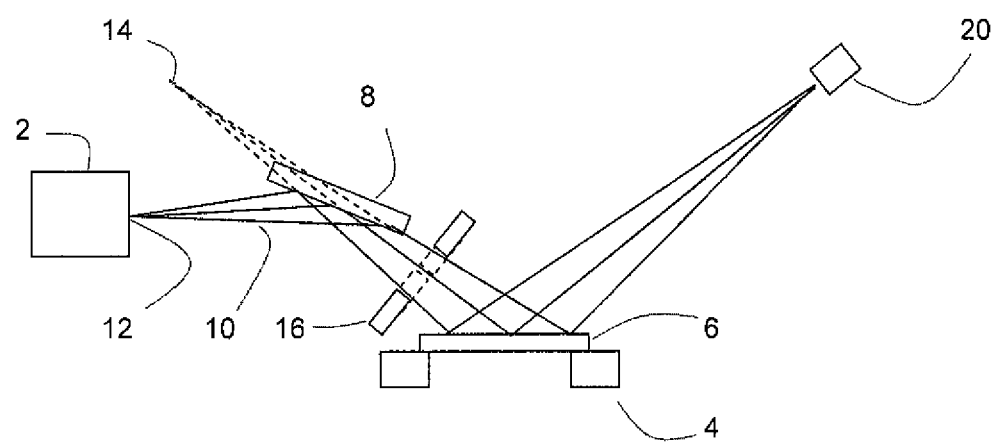
FIG. 2 is a schematic diagram of an arrangement for Bragg-Brentano measurement according to the same embodiment.

To allow for Bragg-Brentano measurements, the geometry is re-arranged to that illustrated in FIG. 2 by rotating the sample stage 4 and the position of detector 20.

The collimator 16 is adjusted to a wider opening illustrated by the full lines in FIG. 2. The narrower slit of FIG. 1 is illustrated using dashed lines in FIG. 2 for comparison.

To ensure the Bragg-Brentano geometry, the apparent focus 14 and the X-ray detector 20 are arranged at the same distance from the sample, referred to as the radius below.

This arrangement delivers a Bragg-Brentano geometry and by using the flat graded multilayer 8 the arrangement can deliver monochromatic X-rays with high intensity, suppression of fluorescent radiation and adjustability for different wavelengths.

Further, the use of the Bragg-Brentano geometry allows for the possible use of a position sensitive detector 20.

It is beneficial to provide the collimator 16 between the flat graded multilayer 8 and the sample stage to allow a larger capture angle of the flat mirror since no additional space is required for the collimator 16 between the source 2 and flat graded multilayer 8. This allows the source 2 and flat graded multilayer 8 to be close and hence the capture angle of the flat mirror can in turn be large. However, in an alternative arrangement the collimator can be arranged between the source 2 and the flat graded multilayer.

The collimator need not be a slit collimator and a two-dimensional collimator may also be used. A two-dimensional collimator may for example collimate the beam suitable for micro-diffraction experiments.

The arrangement has a number of advantages. In particular, the optical design is not restricted to a fixed goniometer radius since the combination of flat graded multilayer 8 and collimator 16 is radius independent—it does not need to be varied as the radius changes.

A key benefit is that there is no need to exchange the incident beam optics or add an additional diffracted beam monochromator when the apparatus is switched between a Bragg-Brentano configuration on the one hand and a measurement configuration for SAXS or reflectometry geometry on the other hand.

Compare this for example with an alternative approach which might be to use a variable divergence slit as an optic for Bragg-Brentano measurements and close this to a small opening for SAXS or reflectivity. However, in such an alternative approach it would not be possible simply to close the collimator to a small opening for SAXS or reflectivity measurements since there would be a need for an additional diffracted beam monochromator.

A further alternative would be to use an incident beam parabolic mirror with an additional collimation system. The use of a parabolic mirror would permit Bragg-Brentano-like geometries but regrettably such an approach would be very limited for Bragg-Brentano powder measurements since it would only be possible to create a Bragg-Brentano like geometry over a small part of the mirror, resulting in a severe intensity loss. If a large irradiated spot was used the increased size of the spot could create a smearing of the reflections, which may strongly reduce the usability of the data—an example is peak overlaps in multi-phase systems.

Accordingly, the approach of the example above using a flat graded multilayer unexpectedly allows the use of the same geometry in both Bragg-Brentano and SAXS measurements.

There is no need for switching mirrors or adding monochromators to adjust the beam path between the different types of measurement greatly easing the ability to switch between measurement approaches and avoiding the need for excessive complexity in the apparatus.

Even if a flat graded multilayer might be proposed for Bragg-Brentano measurements, it has not previously been realised, as far as the inventors are aware, that this approach allows the use of the same configuration also for SAXS or reflectometry.

FIGS. 3 to 6 represent examples of measurements taken using the apparatus according to FIGS. 1 and 2 in comparison with measurements taken on existing conventional instruments.

Figure 3:
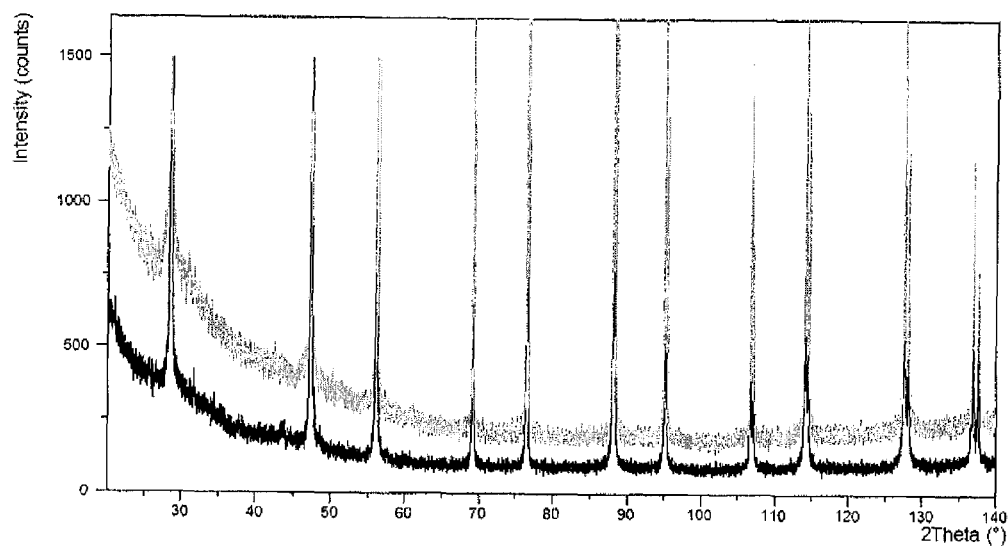
FIG. 3 illustrates Bragg-Brentano results using the arrangement of FIG. 2 and a comparative example.

FIG. 3 shows a Bragg-Brentano measurement of the same powder firstly using a conventional Bragg-Brentano approach and secondly using the arrangement of the invention with a flat graded multilayer. The arrangement using the invention gives significantly reduced background.

Figure 4:
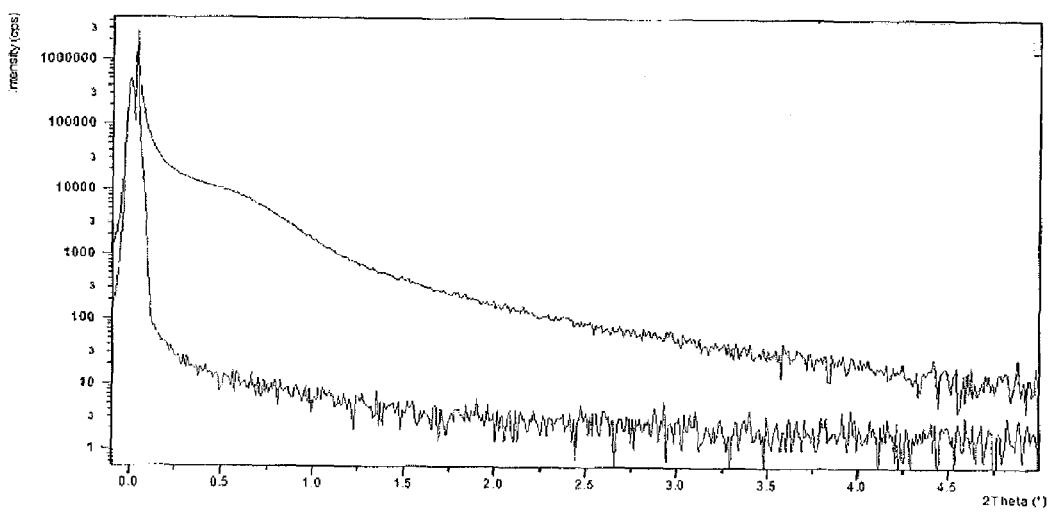
FIG. 4 illustrates SAXS measurements using the arrangement of FIG. 1.

FIG. 4 illustrates the use of the same apparatus for SAXS measurements. In this case, the upper curve is obtained from a sample measurement and the lower curve shows the scan on an empty sample container. The background of the empty sample holder measurement is low and "featureless" down to low 2Theta angles demonstrating the good suitability for SAXS analysis.

Figure 5:
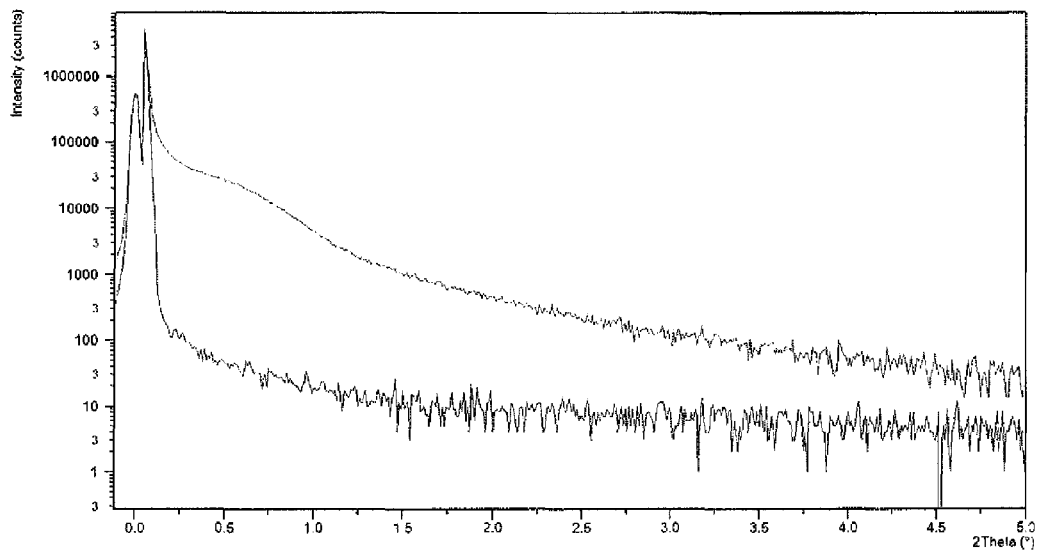
FIG. 5 illustrates SAXS measurements made using a comparative example.

By way of comparison, FIG. 5 shows results on the same sample with another set-up, using a focussing incident beam mirror. It will be seen that the approach of the invention delivers results that are as good as those using a conventional set up.

Figure 6:
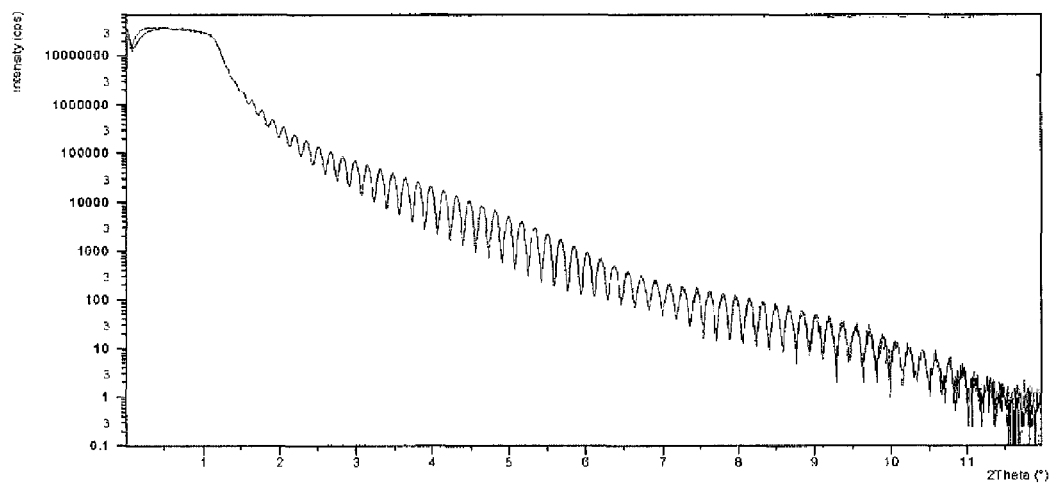
FIG. 6 illustrates reflectometry measurements using the arrangement of FIG. 1 and a comparative example.

FIG. 6 illustrates the use of the same apparatus for reflectometry. In this case, the results are virtually indistinguishable using the apparatus of the invention and using conventional apparatus.

Thus, the arrangement of the invention provides good results for each of Bragg-Brentano measurements, SAXS measurements and reflectometry measurements without requiring significant changes in the apparatus.

The collimator need not be in the form of a single slit.

This may add a collimation in the second dimension, i.e. perpendicular to the collimation in the first direction which allows for additional measurements such as GI-SAXS (gracing incidence SAXS), in-plane diffraction and others.

In particular, with a large aperture in the collimator the set-up is suitable for Bragg-Brentano; with a very narrow slit as aperture it is suitable for SAXS and reflectometry. If in addition to a narrow slit two small masks with slits perpendicular to the narrow slit are placed then this creates not a narrow illumination line of X-rays but a small illuminated area on the sample that could be used for microdiffraction.

Another, more complex way of adding additional collimation is to provide, an additional flat, parabolic, elliptical or hyperbolic shaped multilayer between the flat graded multilayer 8 and the collimator 16, which in this case may be in particular a variable 2D collimator.

These additional arrangements add further flexibility at some cost in the simplicity of the apparatus. However, the basis remains the combination of the flat graded multilayer and one or more collimators.

In some cases, the collimator 16 may be completely removed for Bragg-Brentano measurements and only replaced for SAXS or reflectivity measurements.

Any suitable detector may be used. In particular a two-dimensional X-ray detector with a point spread function smaller than 100 µm by 100 µm may be used to allow a relatively small instrument size.

The above description has focussed on a powder sample but the invention may give good results when used with a wide variety of sample types.

The invention claimed is:

1. X-ray diffraction apparatus, comprising
an X-ray source having a focus;
a sample stage;
a flat graded multilayer between the focus and the sample stage for directing X-rays from the focus onto the sample stage; and
an X-ray detector for detecting X-rays from a sample mounted on the sample stage;
further comprising a collimator located between the X-ray source and the sample stage, wherein the collimator is adjustable to a large effective aperture for Bragg-Brentano geometry measurements and to a narrow effective aperture for SAXS measurements.

2. X-ray diffraction apparatus according to claim 1 wherein the large effective aperture is at least 0.1° and the narrow effective aperture is not greater than 0.07°.

3. X-ray diffraction apparatus according to claim 2 wherein the narrow effective aperture is not greater than 0.05°.

4. X-ray diffraction apparatus according to claim 1 wherein the collimator is located between the flat graded multilayer and the sample stage.

5. X-ray apparatus according to claim 1 wherein the collimator is located between the X-ray source and the flat graded multilayer.

6. X-ray apparatus according to claim 1 wherein the collimator has a slit aperture of variable width.

7. X-ray apparatus according to claim 1 wherein the collimator is a two-dimensional collimator having an aperture of variable width and/or height.

8. X-ray apparatus according to claim 1 further comprising a further flat, parabolic, elliptical or hyperbolic shaped multilayer arranged between the flat graded multilayer and the sample stage.

9. X-ray apparatus according to claim 1 wherein the X-ray detector is a position sensitive detector.

10. A method of operation of X-ray diffraction apparatus comprising an X-ray source having a focus; a sample stage; a flat graded multilayer between the focus and the sample stage for directing X-rays from the focus onto the sample stage; an X-ray detector for detecting X-rays from a sample mounted on the sample stage; and a collimator located between the X-ray source and the sample stage, wherein the collimator is adjustable to a first effective aperture for Bragg-Brentano geometry measurements and to a second effective aperture that is narrower than the first effective aperture for SAXS measurements, the method comprising:
 adjusting the collimator to the first effective aperture and carrying out measurements in a Bragg-Brentano geometry; and
 adjusting the collimator to the second effective aperture and carrying out small angle X-ray scattering, SAXS, measurements.

11. The method according to claim 10 further comprising carrying out reflectometry measurements using the second effective aperture.

12. The method according to claim 10 further comprising carrying out micro-spot analysis measurements using the second effective aperture, wherein the second effective aperture is a two-dimensional aperture.

* * * * *